United States Patent [19]

Smith

[11] Patent Number: 4,917,608

[45] Date of Patent: Apr. 17, 1990

[54] CRANIAL MOTION DENTAL ATTACHMENT

[76] Inventor: Gerald H. Smith, 3569 Cranberry Dr., Huntingdon Valley, Pa. 19006

[21] Appl. No.: 735,141

[22] Filed: May 17, 1985

[51] Int. Cl.$^4$ ............................................. A61C 5/08
[52] U.S. Cl. ..................................... 433/219; 433/169
[58] Field of Search ............... 433/215, 218, 219, 169, 433/180, 181, 170

[56] References Cited

U.S. PATENT DOCUMENTS

| | | | |
|---|---|---|---|
| 1,621,702 | 3/1927 | Yantis | 433/181 |
| 2,227,735 | 1/1941 | Morton | 433/219 |
| 3,083,461 | 4/1963 | Hirschorn | 433/219 |
| 4,332,563 | 1/1982 | Weissman | 433/215 |
| 4,472,142 | 9/1984 | Gedzelman | 433/170 |

Primary Examiner—Robert Peshock
Attorney, Agent, or Firm—N. J. Aquilino

[57] ABSTRACT

A cranial motion dental attachment for linking the interproximal walls of adjacent molded crowns while permitting relative movement therebetween. The attachment includes a piston having an integral retainer stem which is attached to a dental structure and a cylinder attached to an adjacent dental structure adapted to receive the piston so that the piston is moveable within the cylinder permitting horizontal or lateral movement between the adjacent dental pieces.

3 Claims, 1 Drawing Sheet

CRANIAL MOTION DENTAL ATTACHMENT

BACKGROUND OF THE INVENTION

The present invention relates to fixed dental prosthetic devices, and more particularly to cranial motion dental attachments for linking the interproximal walls of adjacent cast crowns while permitting relative movement therebetween.

Before recent developments in cranial studies, little attention was given to the cranial bone structure and the movements therebetween particularly as it concerned the field of dentistry. Dental attachments and prosthetic devices were placed to provide rigid connections between natural teeth and artificial crowns and bridge structures. Advances in craniology have taught that the cranial bones are not rigidly connected, but rather are formed by a series of individual bones interconnected by sutures and that these individual bones move relative to each other during normal body functions such as primary and secondary respiratory motion (breathing), eating and so forth.

Rigid dental attachments directly inhibit this motion causing various reactions generally detrimental to the normal physiologic functions of the cranium, cerebrospinal fluid flow, cranial dural membrane, upper cervical vertebrae, and neuromuscular systems. Rigid attachments also create proprioceptive and physiologic stress between adjacent members of the dental structure which can result in loosening of the supporting structures.

The general problems caused by rigid dental attachments has been addressed in the patents to Morton, 2,129,861 and 2,227,735, and to Weissman, 3,530,582. These patents are directed to lock pins between adjacent dental prosthetic devices and use spherical ball and socket type joints which permit rotational movement between the adjoining structures but do not allow lateral movement.

The present invention is directed to a cranial motion dental attachment which differs from the prior art devices and allows lateral motion between adjacent dental structures. The cranial motion dental attachment was specifically designed for mid-line connections between the maxillary central incisor teeth. The attachment enables horizontal micro-motion of the maxilla as occurs during normal respiratory inhalation while preventing buccal, lingual and gingival torquing forces. The attachment is equally applicable to other sutural locations where cranial micro-motion and normal bone flexibility occurs between adjacent dental structures.

The cranial motion dental attachment takes the form of a piston having an integral retainer body attached to a dental structure and a cylinder attached to an adjacent dental structure adapted to receive the piston so that the piston is moveable within the cylinder permitting horizontal or lateral movement between the adjacent dental structures.

Among the objects of the present invention is the provision of an improved dental prosthetic attachment permitting lateral movement between adjacent dental structures while providing a suitable interconnection between the adjacent dental structures, and the provision of a cranial motion dental attachment which is simple in structure and easily installed in dental prosthetic devices.

Other objects, features and advantages of the present invention will be fully appreciated by referring to the accompanying description of preferred embodiments, as well as the drawings.

DESCRIPTION OF THE PREFERRED EMBODIMENTS

Figure 1:
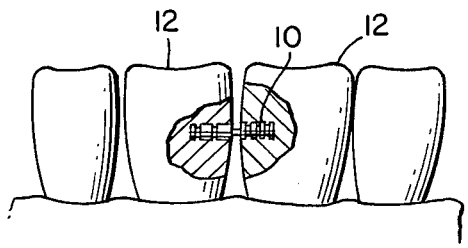
FIG. 1 is a diagrammatic elevational view of a fixed dental prosthetic structure in accordance with the present invention.
Figure 2:
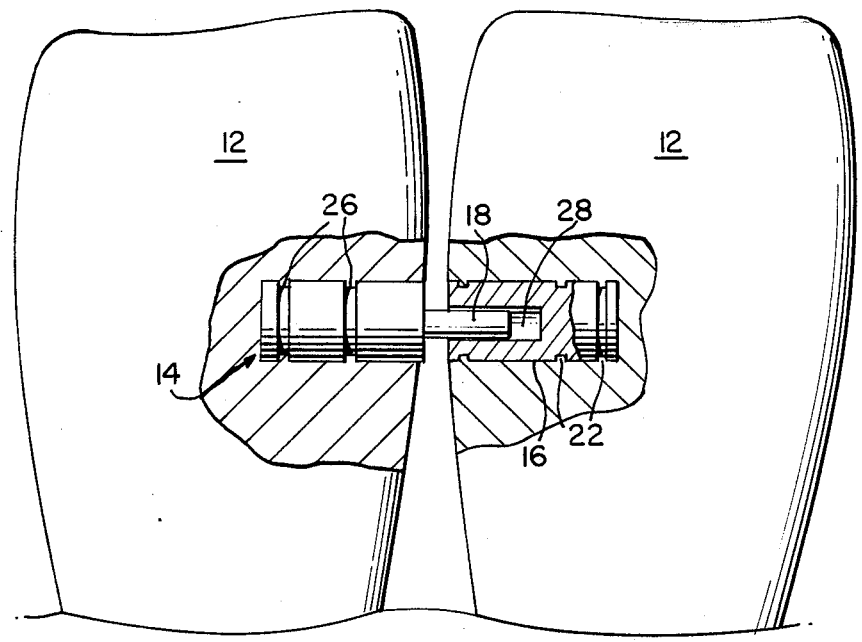
FIG. 2 is a partial elevational view on a greatly enlarged scale, partly in section, showing further structural details of the invention.
Figure 3:
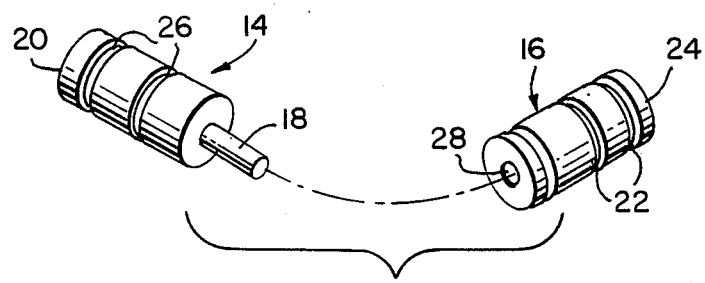
FIG. 3 is an exploded view of the dental attachment of the invention.

Referring to the drawings, and in particular to FIG. 1, the cranial motion attachment 10 is shown with reference to adjacent dental crowns 12. The attachment 10 is preferably positioned in a horizontal manner with respect to the longitudinal axis of the crowns 12. In a preferred embodiment of the attachment, it is formed of two separable and interconnecting pieces 14 and 16. Piece 14 is a cylindrical stainless steel element approximately 7/32 of an inch long and having a one-eighth (⅛) inch diameter piston 18 extending from one end thereof. Piece 14 includes a retaining body 20 having a plurality of annular retention grooves 22 machined in its surface as shown. As shown in FIG. 2, the body 20 is embedded within the crown up to the end thereof so that the piston 18 projects horizontally from the crown surface. Piece 16 is also formed with a retention body 24 and includes a series of annular retention grooves 26. A cylindrical bore 28 is provided in the end of the piece 16 and is adapted to receive the piston 18. The size of the piston and the corresponding size of the bore 28 is designed to provide a close tolerance between the piston 18 and bore 28 while permitting relative movement therebetween. In a preferred embodiment, the piston is 0.054 inches in diameter and the bore is 0.055 inches in diameter. As shown in FIG. 2, piece 16 is also embedded in an adjacent crown so that the end of the piece lies substantially planer to the surface of the crown. When the crowns are in place, as shown in FIGS. 1 and 2, the pieces 14 and 16 are adapted to abut each other as the piston 18 is received within the bore 28.

With this arrangement, it can be seen that adjacent crown members of a dental structure can be attached while at the same time permitting horizontal or lateral movement between the members thereby eliminating the problems with conventional rigid connections.

It will be appreciated that modifications may be made in the above invention without departing from the scope of the invention. For example, the cranial motion dental attachment may be fabricated in several different metals including gold alloy, palladium, chrome cobalt and stainless steel.

What I claim is:

1. A cranial motion dental attachment for linking interproximal wall of adjacent molded crowns while permitting relative movement therebetween, comprising; a first member adapted to be mounted within a first dental crown having a cylindrical piston integrally connected to and extending from one end thereof; and a second member adapted to be mounted in a second dental crown adjacent said first dental crown; said second member including a cylindrical bore formed therein and adapted to receive said piston, in use, permitting relative movement between said first and second members.

2. A cranial motion dental attachment for linking interproximal walls of adjacent molded crowns while permitting relative motion therebetween, comprising; a first member adapted to be mounted within a first dental crown, said first member including a cylindrical body and a cylindrical piston integrally connected with said body and extending from one end thereof; and a second member adapted to be mounted in a second dental crown adjacent said first dental crown; said second member including a cylindrical retention body and a cylindrical bore formed therein, said bore adapted to receive said piston, in use, permitting relative movement between said first and said second members.

3. The dental attachment of claim 2 wherein said first and second members further include annular retention rings formed on each of said cylindrical retention bodies.

* * * * *